US011964286B2

(12) United States Patent
Stanton et al.

(10) Patent No.: US 11,964,286 B2
(45) Date of Patent: Apr. 23, 2024

(54) CELL WASHING CHAMBER FOR BLOOD PROCESSING CENTRIFUGE

(71) Applicant: Terumo BCT, Inc., Lakewood, CO (US)

(72) Inventors: Briden Ray Stanton, Highlands Ranch, CO (US); Ryan D. Rykhus, Boulder, CO (US); Rachel Michelle Von Seggern, Johnstown, CO (US); Ashely Ann Marcolina, Arvada, CO (US)

(73) Assignee: Terumo BCT, Inc., Lakewood, CO (US)

( * ) Notice: Subject to any disclaimer, the term of this patent is extended or adjusted under 35 U.S.C. 154(b) by 902 days.

(21) Appl. No.: 16/842,205

(22) Filed: Apr. 7, 2020

(65) Prior Publication Data
US 2020/0324301 A1 Oct. 15, 2020

Related U.S. Application Data

(60) Provisional application No. 62/833,051, filed on Apr. 12, 2019.

(51) Int. Cl.
B04B 7/08 (2006.01)
A61M 1/36 (2006.01)
(Continued)

(52) U.S. Cl.
CPC ........... *B04B 7/08* (2013.01); *A61M 1/36224* (2022.05); *A61M 1/36225* (2022.05);
(Continued)

(58) Field of Classification Search
CPC .. B04B 7/08; B04B 1/02; B04B 15/12; B04B 2005/0471; B04B 5/0442; C12M 47/02;
(Continued)

(56) References Cited

U.S. PATENT DOCUMENTS 2,616,619 A 11/1952 MacLeod
3,391,597 A 7/1968 Gropper
(Continued)

FOREIGN PATENT DOCUMENTS

DE 2658926 A1 6/1978
DE 2701976 A1 7/1978
(Continued)

OTHER PUBLICATIONS

Figdor et al, "Theory and Practice of Centrifugal Elutriation (CE), Factors Influencing the Separation of Human Blood Cells", Cell Biophysics 5, 1983, 105-118.
(Continued)

*Primary Examiner* — Walter D. Griffin
*Assistant Examiner* — Shuyi S. Liu
(74) *Attorney, Agent, or Firm* — Harness, Dickey & Pierce, P.L.C.

(57) ABSTRACT

A frustro-conical chamber for separating particles in a fluidized bed for blood component or cell separation. The chamber is characterized by an injection-directing surface for directing inflowing fluid along a frustro-conical wall of the chamber. A dam adjacent the cell-injection port may be circumferentially disposed within the chamber and may have its maximum height adjacent an injection port, and the height may diminish away from the injection port. The injection directing surface may comprise a shelf extending into the interior of the chamber from the injection port, thereby impeding fluid flow in the direction of an outlet port.

19 Claims, 11 Drawing Sheets

(51) Int. Cl.
*B04B 1/02* (2006.01)
*B04B 15/12* (2006.01)
*C12M 1/00* (2006.01)

(52) U.S. Cl.
CPC ......... *A61M 1/362265* (2022.05); *B04B 1/02* (2013.01); *B04B 15/12* (2013.01); *C12M 47/02* (2013.01)

(58) Field of Classification Search
CPC .. C12M 47/04; B01D 2221/10; B01D 21/262; A61M 1/3696
See application file for complete search history.

(56) References Cited

U.S. PATENT DOCUMENTS

| | | | |
|---|---|---|---|
| 3,987,961 A | 11/1976 | Sinn et al. | |
| 4,187,979 A | 2/1980 | Cullis et al. | |
| 4,256,120 A | 3/1981 | Finley | |
| 4,443,345 A | 4/1984 | Wells | |
| 4,720,284 A | 1/1988 | McCarty | |
| 4,939,087 A | 7/1990 | Van Wie et al. | |
| 4,990,132 A | 2/1991 | Unger et al. | |
| 5,039,401 A | 8/1991 | Columbus et al. | |
| 5,405,308 A | 4/1995 | Headley et al. | |
| 5,577,513 A | 11/1996 | Van Vlasselaer | |
| 5,674,173 A | 10/1997 | Hlavinka et al. | |
| 5,722,926 A | 3/1998 | Hlavinka et al. | |
| 5,792,372 A | 8/1998 | Brown et al. | |
| 5,858,251 A | 1/1999 | Borchardt et al. | |
| 5,906,570 A | 5/1999 | Langley et al. | |
| 5,913,768 A | 6/1999 | Langley et al. | |
| 5,939,319 A | 8/1999 | Hlavinka et al. | |
| 5,951,877 A | 9/1999 | Langley et al. | |
| 6,022,306 A | 2/2000 | Dumont et al. | |
| 6,051,146 A | 4/2000 | Green et al. | |
| 6,053,856 A | 4/2000 | Hlavinka | |
| 6,071,422 A | 6/2000 | Hlavinka et al. | |
| 6,334,842 B1 | 1/2002 | Hlavinka et al. | |
| 6,352,499 B1 | 3/2002 | Geigle | |
| 6,354,986 B1 | 3/2002 | Hlavinka et al. | |
| 6,514,189 B1 | 2/2003 | Hlavinka et al. | |
| 6,574,173 B1 | 6/2003 | Manes | |
| 6,616,019 B2 | 9/2003 | D'Alessio et al. | |
| 7,029,430 B2 | 4/2006 | Hlavinka et al. | |
| 7,201,848 B2 | 4/2007 | Antwiler et al. | |
| 7,549,956 B2 | 6/2009 | Hlavinka et al. | |
| 7,588,692 B2 | 9/2009 | Antwiler et al. | |
| 7,857,744 B2 | 12/2010 | Langley et al. | |
| 7,963,901 B2 | 6/2011 | Langley et al. | |
| 8,066,888 B2 | 11/2011 | Sweat et al. | |
| 8,226,537 B2 | 6/2012 | Pittinger et al. | |
| 8,992,402 B2 | 3/2015 | Holmes | |
| 2003/0116512 A1 | 6/2003 | Antwiler et al. | |
| 2005/0051466 A1 | 3/2005 | Carter et al. | |
| 2006/0086675 A1 | 4/2006 | Purdum | |
| 2006/0147895 A1 | 7/2006 | Purdum | |
| 2007/0102374 A1 | 5/2007 | Kolenbrander | |
| 2008/0318756 A1 | 12/2008 | Langley et al. | |
| 2012/0316049 A1 | 12/2012 | Holmes et al. | |
| 2012/0316051 A1 | 12/2012 | Holmes et al. | |
| 2013/0203582 A1 | 8/2013 | Katz | |
| 2016/0045921 A1* | 2/2016 | Taga | B04B 5/0442 494/37 |

FOREIGN PATENT DOCUMENTS

| | | |
|---|---|---|
| DE | 3700122 A1 | 7/1988 |
| DE | 3734170 A1 | 4/1989 |
| EP | 0406485 A1 | 1/1991 |
| EP | 0408462 B1 | 6/1995 |
| WO | 87/06857 | 11/1987 |
| WO | 96/33203 | 10/1996 |
| WO | 98/18403 | 5/1998 |
| WO | 2008051847 A2 | 5/2008 |
| WO | 2012173754 A1 | 12/2012 |
| WO | 2012174007 A1 | 12/2012 |

OTHER PUBLICATIONS

Grabske, Robert, "Separating Cell Populations by Elutriation", Beckman Instruments, 1978, pp. 1-8.

Lutz et al, "Large-Scale Cell Separation by Cenuifugal Elutriation", Analytical Biochemistry, 1992, 200:376-380.

Sanderson et al, "Design Principles for a Counterflow Centrifugation Cell Separation Chamber", Analytical Biochemistry, 1976, 71:615-622.

Tulp et al, "A Separation Chamber to Sort Cells and Cell Organelles by Weak Physical Forces. V.A. Sector-Shaped Chamber and Its Application to the Separation of Peripheral Blood Cells", J. of Immunological Methods, 1984, 69:281-295.

International Search Report and Written Opinion, PCT/US2020/027052, dated Jul. 3, 2020.

* cited by examiner

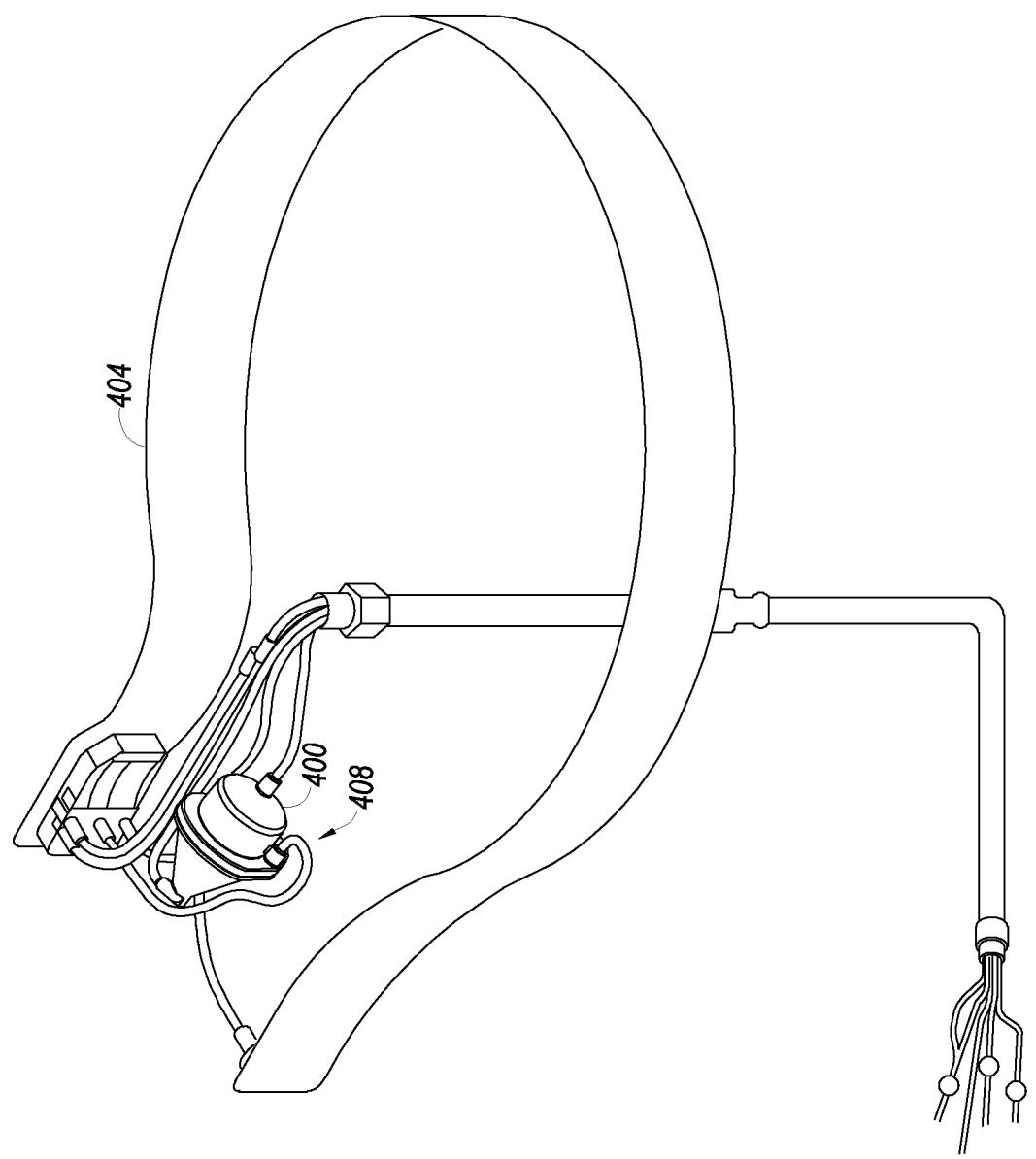

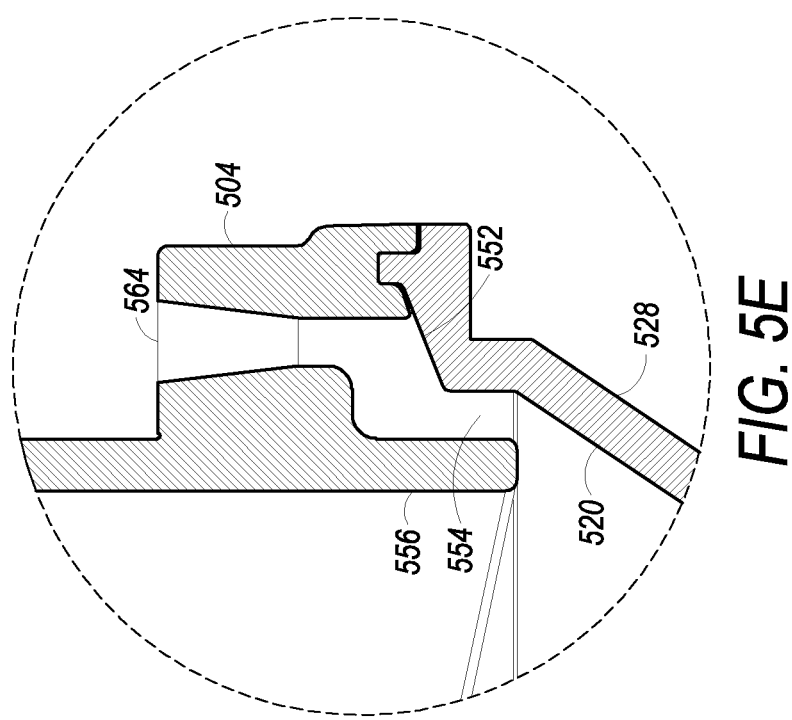
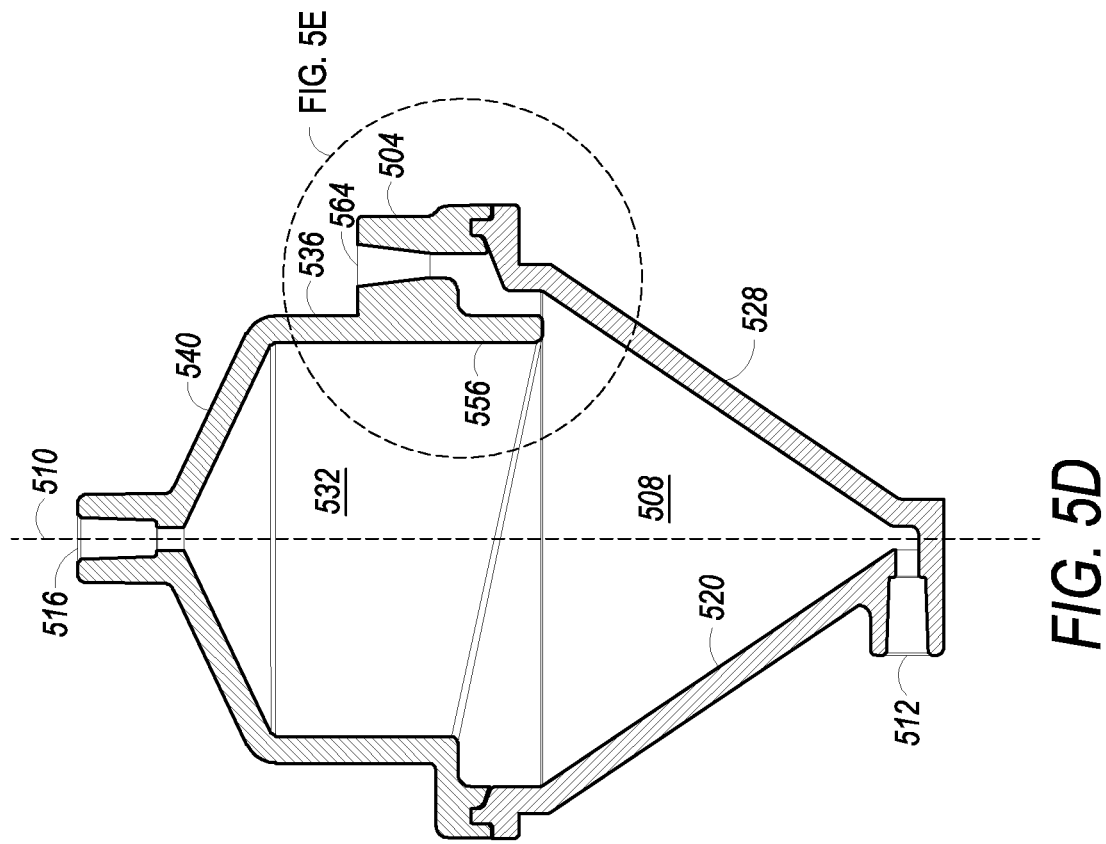

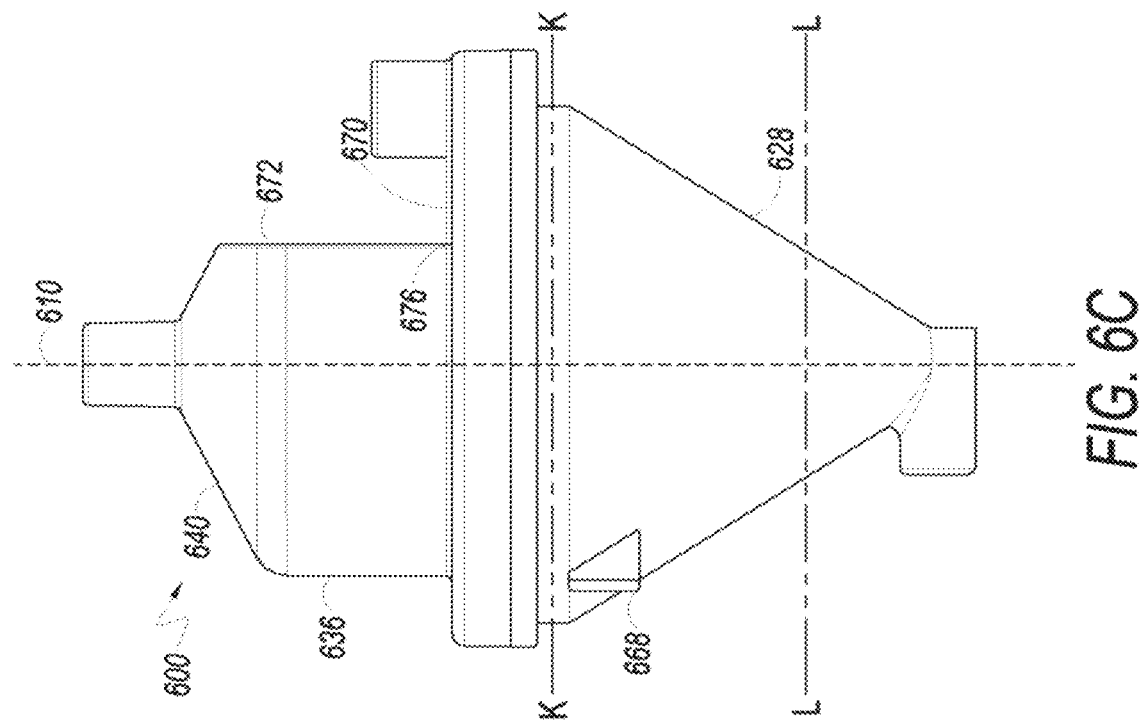
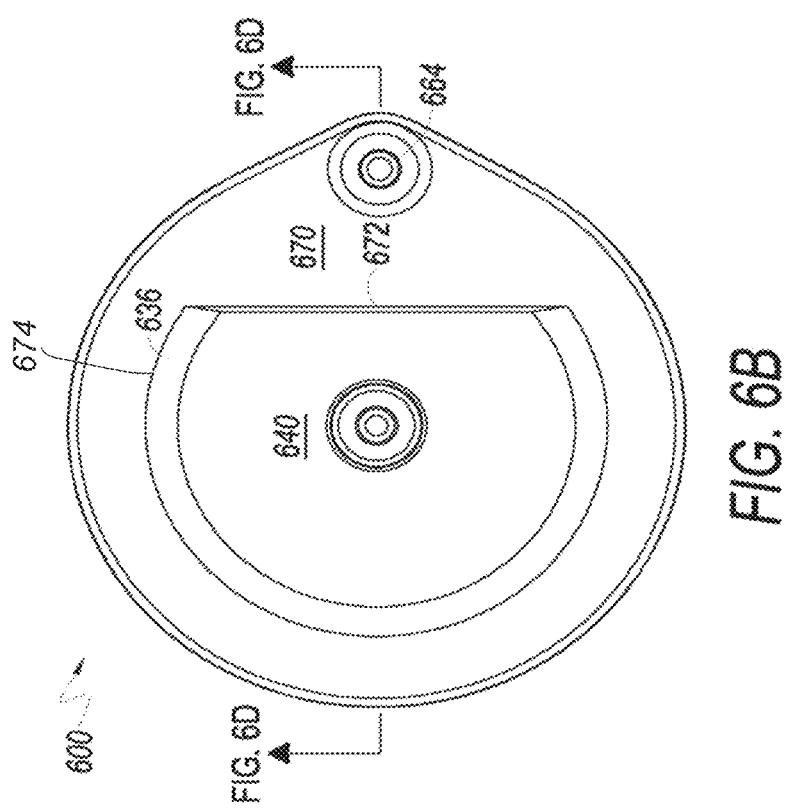

CELL WASHING CHAMBER FOR BLOOD PROCESSING CENTRIFUGE

BACKGROUND

Several processes require the concentration of particles. Particles may be suspended or carried in a first liquid and for additional processing, it may be useful to remove or dilute the first liquid by washing the particles with a second liquid. For example, within the biological sciences there exists a need for washing cells. One example where this is necessary is where cellular components of blood, e.g., leukocytes, erythrocytes, thrombocytes, are separated from other liquid components such as plasma. Another example is the post processing of cells that may be grown in a liquid medium for therapeutic or research purposes. The cells may be separated with respect to the liquid medium in which they are grown. The separation or concentration of the cells must occur without having a significant effect on their viability for later use.

Embodiments of the present invention have been made in light of these and other considerations. However, the relatively specific problems discussed above do not limit the applicability of the embodiments of the present invention.

US 2016/045921A1, incorporated herein by reference, relates to apparatuses, systems, and methods for processing particles by washing, concentrating, and or treating the particles. Some embodiments provide for a chamber that includes an entry port for introducing a first liquid and particles into a volume of the chamber. The chamber also includes a first exit port, located below the entry port, for removing the particles from the volume of the chamber after the particles have been processed. In some embodiments, a liquid may be introduced into the chamber volume through the first exit port in order to perform some processing steps, e.g., washing of the particles. A second exit port of the chamber is located above the first exit port and is utilized for removing liquid from the volume of the chamber. The chamber also includes a sloped surface that directs at least a portion of the particles, introduced into the volume, toward the first exit port.

SUMMARY

The summary is provided to introduce aspects of some embodiments of the present invention in a simplified form and is not intended to identify key or essential elements of the claimed invention, nor is it intended to limit the scope of the claims.

The present disclosure is directed to a frustro-conical chamber for separating particles in a fluidized bed. The chamber is adapted for use in a blood component or cell separation system comprising a disposable set of tube-connected bags and a centrifuge system. The chamber has an inlet/evacuation port at an apex of the frustro-conical chamber and an outlet port at a base of the chamber. A cell-injection port is located between the apex and the base on a side of the chamber and is oriented to direct inflowing cell-containing fluid toward the inlet/evacuation port.

The chamber is characterized by injection-directing means for directing inflowing fluid along a frustro-conical wall of the chamber.

The injection directing means may comprise, in one embodiment, a dam adjacent the cell-injection port. The dam may be circumferentially disposed within the chamber and forms a channel between the dam and the frustro-conical chamber. The dam may have its maximum height adjacent the injection port, and the height may diminish away from the injection port on at least one side of the injection port or on both sides thereof. The dam may extend partially around the circumference of the chamber or completely around the circumference, with the channel ending at a point diametrically across the chamber from the injection port. The height of the dam may also decrease uniformly away from the cell-injection port.

In another embodiment, the injection directing means may comprise a shelf. The shelf may extend into the interior of the chamber from the injection port, thereby impeding fluid flow in the direction of the outlet port. The shelf may be generally planar and may be coupled to the wall of the chamber at a curved edge of the shelf. The curved edge may be perpendicular to an axis of the chamber. The axis may be defined as a line from the inlet/evacuation port to the outlet port. The self may also comprise an interior edge extending between two ends of the curved edge. The interior edge may be straight. The chamber may also comprise a truncation wall coupled to the interior edge of the shelf and perpendicular to the shelf. The truncation wall prevents cell-containing fluid from becoming trapped on a side of the shelf facing the outlet port. The truncation wall may be planar.

In a further embodiment, the injection-directing means may be comprised of both a dam, as heretofore described, and a shelf.

BRIEF DESCRIPTION OF THE DRAWINGS

FIG. 4 illustrates a liquid processing vessel and an embodiment of a chamber that may be used in combination in some embodiments.

FIGS. 5A-E illustrate views of a chamber consistent with a first embodiment.

FIGS. 6A-D illustrate views of a chamber consistent with a second embodiment.

DETAILED DESCRIPTION

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Embodiments below may be described with respect to processing cells such as by separating cells from other cells or liquid components, concentrating cells, and/or washing cells. However, this is done simply for illustrative purposes. It is noted that the embodiments are not limited to the description below. The embodiments are intended for use in products, processes, devices, and systems that process organic or inorganic particles, particulates, agglomerates. Accordingly, embodiments are not limited to separation, concentration, or washing of cells, e.g., cellular components in whole blood, but may be used to separate any particle from any liquid.

Figure 1:
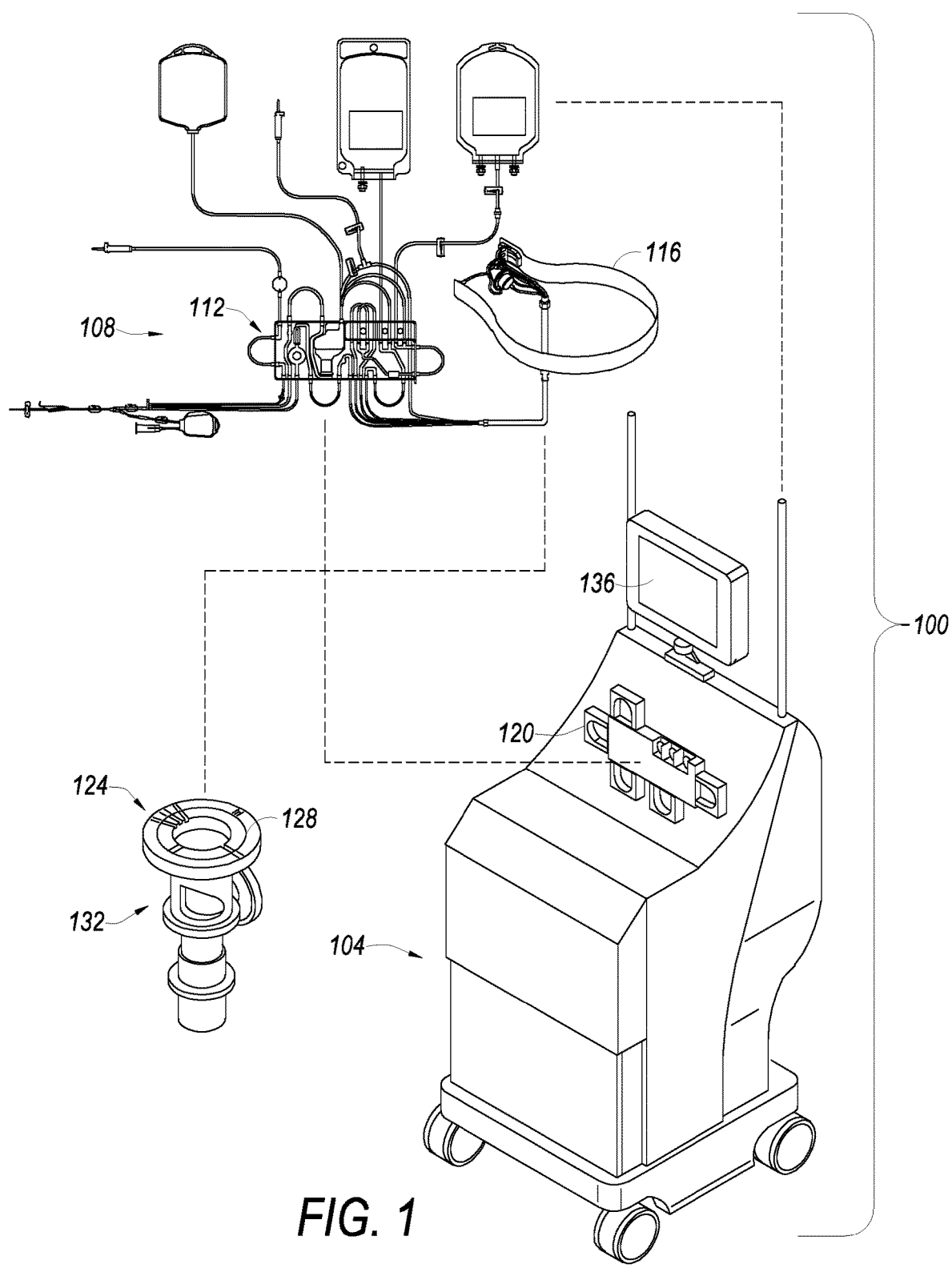
FIG. 1 illustrates an embodiment of a separation system, which can be used in, or with, embodiments.

FIG. 1 illustrates one embodiment of a separation system 100, which can be used in, or with, embodiments. In some embodiments, separation system 100 provides for a continuous whole blood separation process. In other embodiments, separation system 100 provides for concentrating and washing cells. In one embodiment, whole blood is withdrawn from a donor and is substantially, continuously provided to a separation device 104 where the blood is separated into various components and at least one of these components is collected from the device 104. One or more of the separated components may be either collected for subsequent use or returned to the donor. In embodiments, blood is withdrawn from the donor and directed through a bag and tubing set 108, which includes a tubing circuit 112, and a liquid processing vessel 116, which together define a closed, sterile and disposable system. The set 108 is adapted to be mounted in the separation device 104. The separation device 104 includes a pump/valve/sensor assembly 120, which interfaces with the tubing circuit 112, and a centrifuge assembly 124, which interfaces with the liquid processing vessel 116.

In another embodiment, a volume of cells in liquid (e.g., suspended or carried in liquid) is withdrawn from a storage container and is substantially, continuously provided to separation device 104 where the cells are collected from the device 104 after concentrating and/or washing. Additional liquid from processing the volume of cells in liquid may be discarded. In embodiments, a bag with the volume of cells and liquid may be directed through tubing set 108, which includes a tubing circuit 112, and a liquid processing vessel 116, which together define a closed, sterile and disposable system. The set 108 is adapted to be mounted in the separation device 104, as noted above.

Examples of separation systems that may be the basis of systems used with embodiments of the present invention, e.g., separation system 100, include the SPECTRA OPTIA® apheresis system, COBE® spectra apheresis system, and the TRIMA ACCEL® automated blood collection system, all manufactured by Terumo BCT, Inc. of Lakewood, Colo.

The centrifuge assembly 124 may include a channel 128 in a rotatable rotor assembly 132 (e.g., centrifuge), where the channel 128 may be used to hold a liquid processing vessel, e.g., vessel 116. The rotor assembly 132 may rotate to create a centrifugal field. The rotor assembly 132 may be configured to hold a chamber used to separate, concentrate, and/or wash cells. In one example, when whole blood is processed, cellular components of blood may be separated from each other and from liquid components of blood. In other examples, a volume of liquid containing cells may be processed with centrifuge assembly 124 to concentrate the volume of cells.

The liquid processing vessel 116 may be fitted within the channel 128. In one example, blood can flow substantially continuously from a donor, through the tubing circuit 112, and into the rotating liquid processing vessel 116. Within the liquid processing vessel 116, blood may be separated into various blood component types and at least one of these blood component types (e.g., white blood cells, platelets, plasma, or red blood cells) may be removed from the liquid processing vessel 116 and further processed. Blood components that are not being retained for collection or for therapeutic treatment (e.g., platelets and/or plasma) may also be removed from the liquid processing vessel 116 and returned to the donor via the tubing circuit 112.

In another example, a relatively large volume of liquid containing particles (e.g., cells) may be preprocessed using the liquid processing vessel 116. The volume of liquid and cells may be initially flowed into the liquid processing vessel 116 from tubing circuit 112. Within the liquid processing vessel 116, at least a portion of the liquid may be separated from the particles and removed from the liquid processing vessel 116 through tubing circuit 112. A portion of the cells and liquid may be retained for further processing.

Various alternative systems (not shown) may also be used with embodiments of the present invention, including batch processing systems or smaller scale batch or continuous separation systems.

Operation of the separation device 104 may be controlled by one or more processors included therein, and may comprise a plurality of embedded computer processors that are part of a computer system. The computer system may also include components that allow a user to interface with the computer system, including for example, memory and storage devices (RAM, ROM (e.g., CD-ROM, DVD), magnetic drives, optical drives, flash memory); communication/networking devices (e.g., wired such as modems/network cards, or wireless such as Wi-Fi); input devices such keyboard(s), touch screen(s), camera(s), and/or microphone(s); and output device(s) such as display(s), and audio system(s). In order to interface with an operator of the system 100, embodiments of the separation device 104 may include a graphical user interface 136 (shown in FIG. 1) with a display that includes an interactive touch screen.

Figure 2:
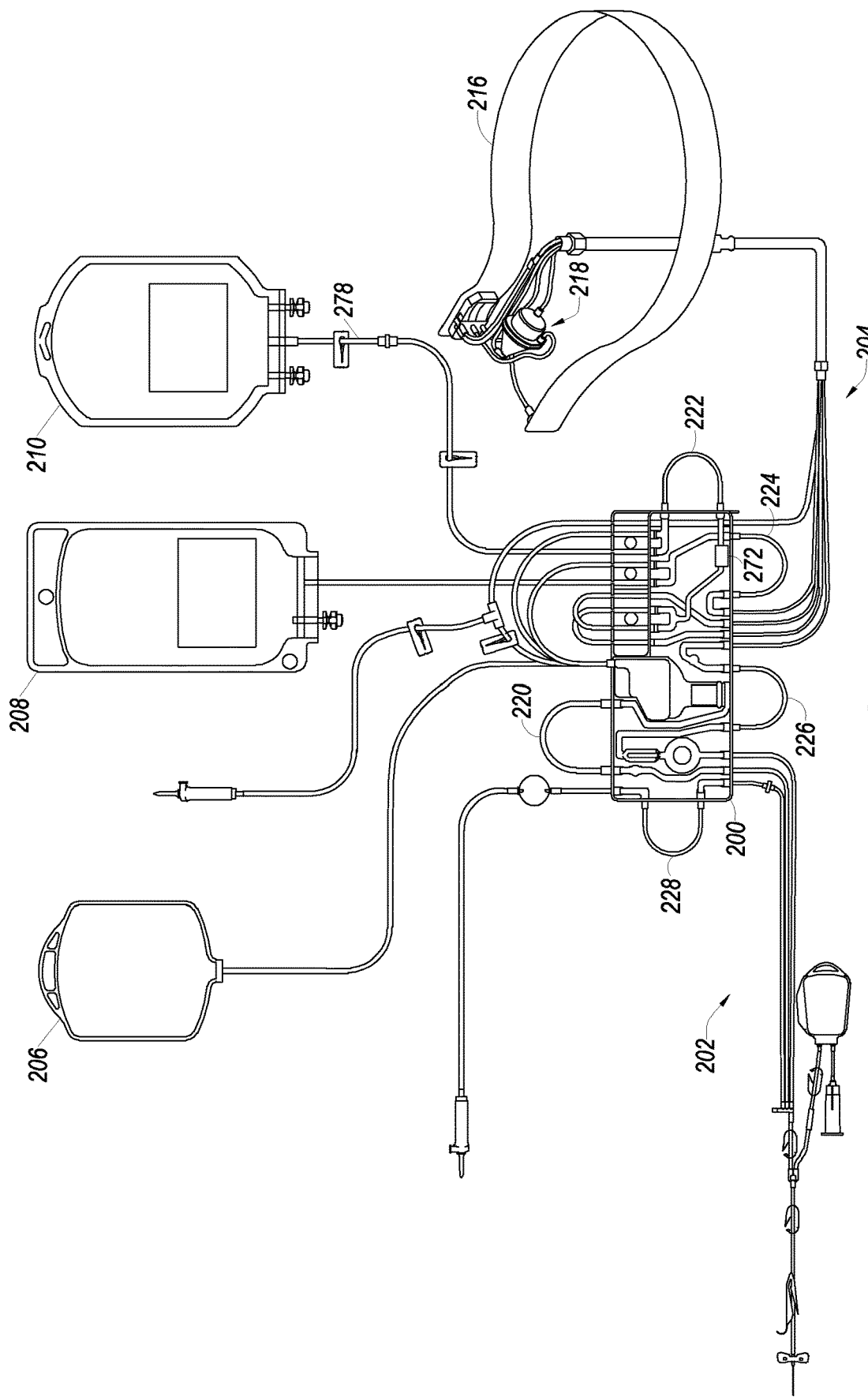
FIG. 2 illustrates a tubing and bag set for use in, or with, embodiments of the present invention.

An embodiment of a tubing circuit that may be used with embodiments is shown in FIG. 2, and as shown may include a cassette 200 and a number of tubing/storage assemblies 202, 204, 206, 208, and 210. In addition, tubing loops 220, 222, 224, 226, and 228 may engage with peristaltic pumps on a separation device, e.g., device 104, to pump fluids through the tubing/storage assemblies. The tubing circuit also includes chamber 218.

In embodiments, the tubing circuit shown in FIG. 2 may be used to separate whole blood into components. In embodiments, some components separated from whole blood may be returned to a donor, stored in one or more storage containers, or further processed. For example, whole blood may be circulated through tubing of the tubing circuit and into the liquid processing vessel 216, which is mounted on a rotor assembly (e.g., assembly 128). Chamber 218 may also be mounted on the rotor assembly.

In the liquid processing vessel 216, the blood may separate into components. Some components may be returned to a donor while others may be further processed. For example, chamber 218 may be used to further process (concentrate or wash components of whole blood). In one embodiment, red blood cells separated from whole blood may be introduced into chamber 218 and concentrated before being stored in a container, e.g., a bag. In other embodiments, the red blood cells may be washed or treated inside chamber 218, in addition to being concentrated, before being stored in a container. As another example, platelets may be directed to chamber 218 where they may be further processed (concentrated, washed, treated, etc.) before being stored in a container. Examples of chambers that may be used as chamber 218 in some embodiments are described in greater detail below, including description of some chamber designs that have entry ports and exit ports in specific locations (FIGS. 5A-7).

Figure 3:
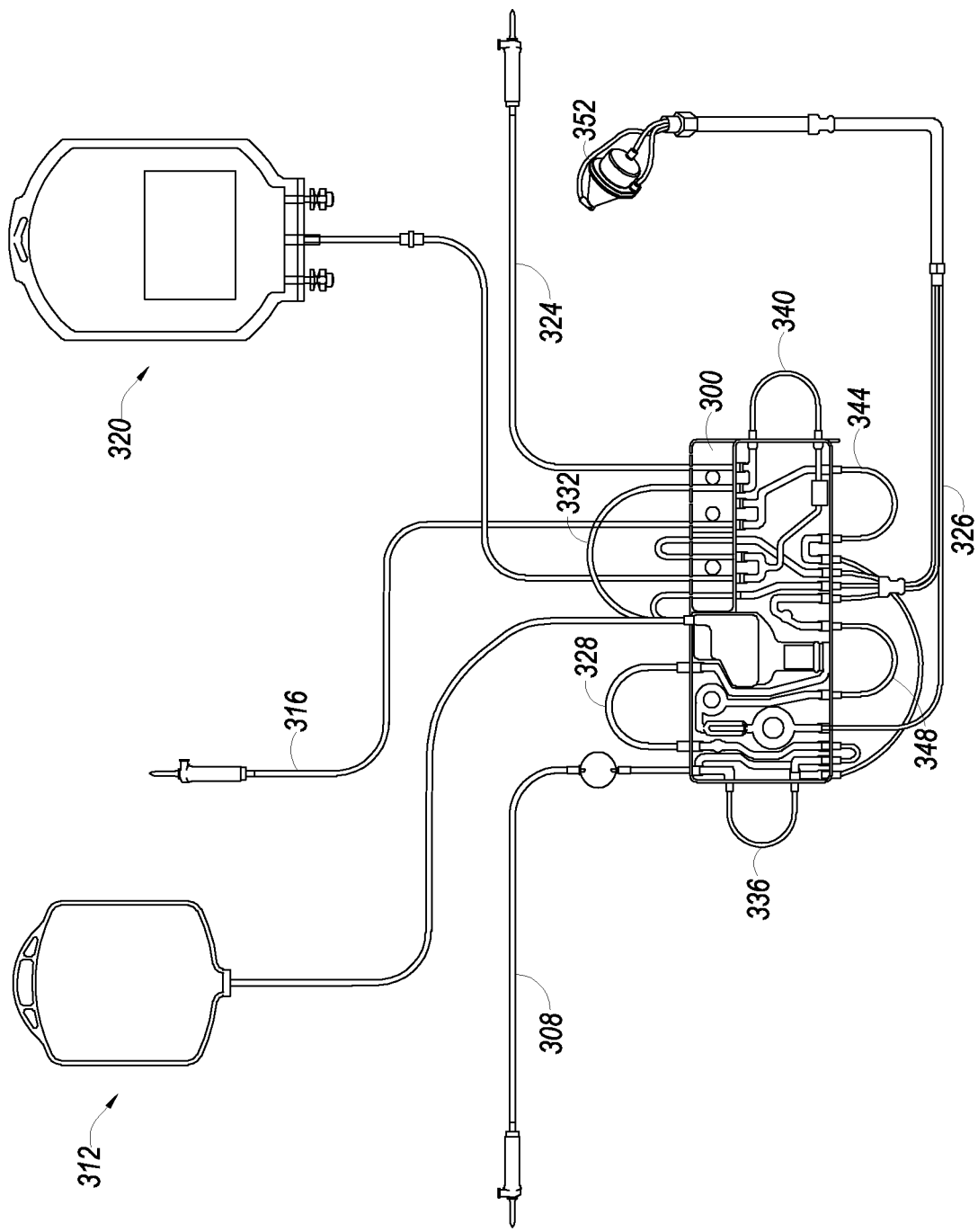
FIG. 3 illustrates another example of a tubing and bag set for use in, or with, embodiments.

Another embodiment of a tubing circuit that may be used with embodiments is shown in FIG. 3. The tubing circuit includes a cassette 300 and a number of tubing/storage assemblies 308, 312, 316, 320, 324, and 326. In addition, tubing loops 328, 332, 336, 340, 344, and 348 may engage with peristaltic pumps to pump fluids through cassette 300 and the tubing/storage assemblies. Assembly 312 provides a vent container, e.g., bag that allows air displaced by liquid flowing in the tubing circuit to be discharged into the vent container. The tubing circuit also includes a chamber 352. Examples of chambers that may be used as chamber 352 in some embodiments are described in greater detail below (FIGS. 5A-7).

In embodiments, the tubing circuit shown in FIG. 3 may be used to concentrate a volume of particles, e.g., cells, in liquid. In embodiments, the tubing circuit may be mounted on a separation device so that chamber 352 is mounted on a rotor assembly (e.g., assembly 128 with a centrifuge), which rotates the chamber 352.

Initially, a container storing the volume of particles with liquid may be attached to tubing assembly 316. The particles in liquid may flow through tubing in the tubing circuit and into chamber 352. As described in greater detail below, some embodiments provide for specific chamber designs that have entry ports and exit ports in specific locations. As the chamber 352 rotates, it may separate some liquid from the particles and the removed liquid may flow through tubing into a container, e.g., a waste bag in assembly 320.

In some embodiments, the particles, in addition to being concentrated, may be washed or treated. In these embodiments, a wash or treatment liquid storage container may be attached to tubing assembly 308. The wash or treating liquid may flow through tubing into chamber 352 to wash or treat the particles after, or during, concentration. The used wash or treatment fluid may flow out of chamber 352 and into waste bag assembly 320.

After the particles have been processed (concentrated, washed, and/or treated), they may flow from chamber 352 through tubing in the tubing circuit and through tubing assembly 324. In some embodiments, a storage container may be attached to tubing assembly 324 to store the processed particles. In other embodiments, tubing assembly 324 may be attached to an inlet of other tubing sets that are used to further process the particles.

In some embodiments, the tubing circuit shown in FIG. 3 may include some additional components. For example, shown in FIG. 4 is a chamber 400 (which may be similar to chamber 352), connected to a liquid processing vessel 404 (which may be similar to vessel 216). In some embodiments, the liquid processing vessel 404 may be used for preprocessing of a volume of particles in liquid prior to processing in chamber 400.

As one example, if the volume of liquid with particles is relatively large, or it is desireable to process the volume at a high flow rate, it may not be possible to process the volume directly by chamber 400. In these embodiments, vessel 404 may be used in a preprocessing step that allows larger volumes (or flow rates) of liquid to be processed. For example, a centrifuge assembly (e.g., assembly 124) may include a channel in a rotatable rotor assembly (e.g., centrifuge), where the channel may be used to hold the liquid processing vessel 404. The rotor assembly may rotate to create a centrifugal field. The rotor assembly may also be configured to hold chamber 400.

Liquid (with the particles) may flow into vessel 404 through port 408. As the liquid flows around the vessel 404, which is rotating, liquid with the particles may separate from other liquid that does not include the particles, creating a concentrated volume of particles and liquid. The separated liquid (without particles) may be directed to a waste bag, with the a more concentrated stream of liquid and particles flowing into chamber 400, where the particles may be further concentrated, washed, and/or treated.

FIGS. 2-4 illustrate some embodiments of tubing circuits with chambers and vessels that are consistent with embodiments of the present invention. In embodiments, the tubing circuits of FIGS. 2-4 can be disposable so that they are used one time to process a volume of liquid, e.g., blood, cells in growing medium, cells in storage medium etc., and then discarded. In other embodiments, the tubing circuits can be reposable (reused) or include one or more component(s) that are reposable.

It is noted that the present invention is not limited to the specific tubing circuit configurations shown in FIGS. 2-4 and described above. Other tubing assembly arrangements, including additional components not shown in FIGS. 2-4 may be utilized in embodiments. For example, in some embodiments a tubing circuit may combine features of FIG. 3 and FIG. 4 and include additional tubing that provides flow paths to the various components.

FIGS. 5A-7 illustrate chambers 500, 600, 700 that may be used for processing particles, e.g., concentrate, wash, and/or treat particles in a liquid, such as cells in a liquid medium.

Figure 5A:
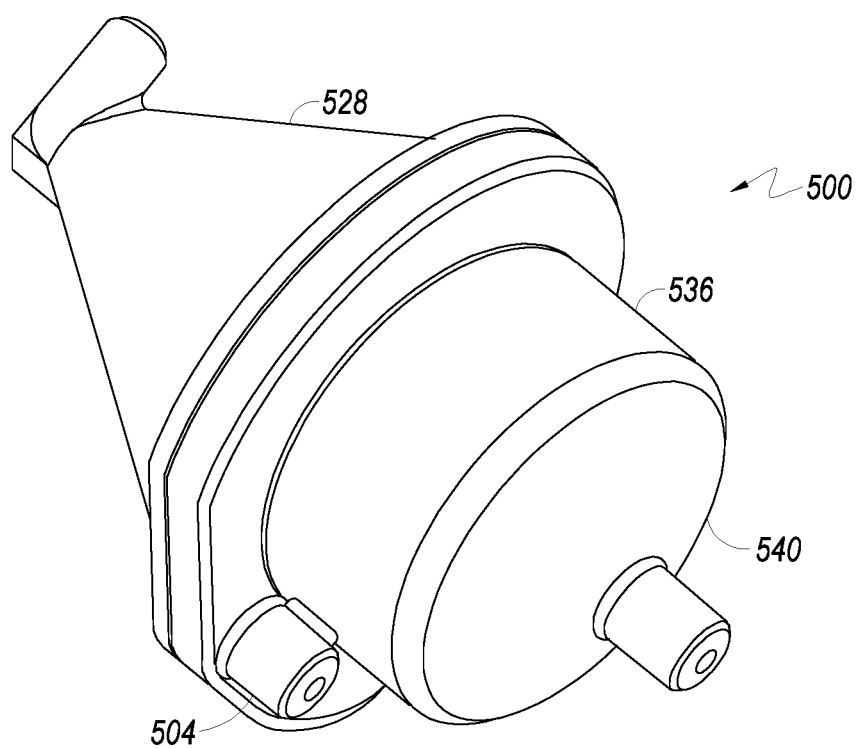
Figure 5C:
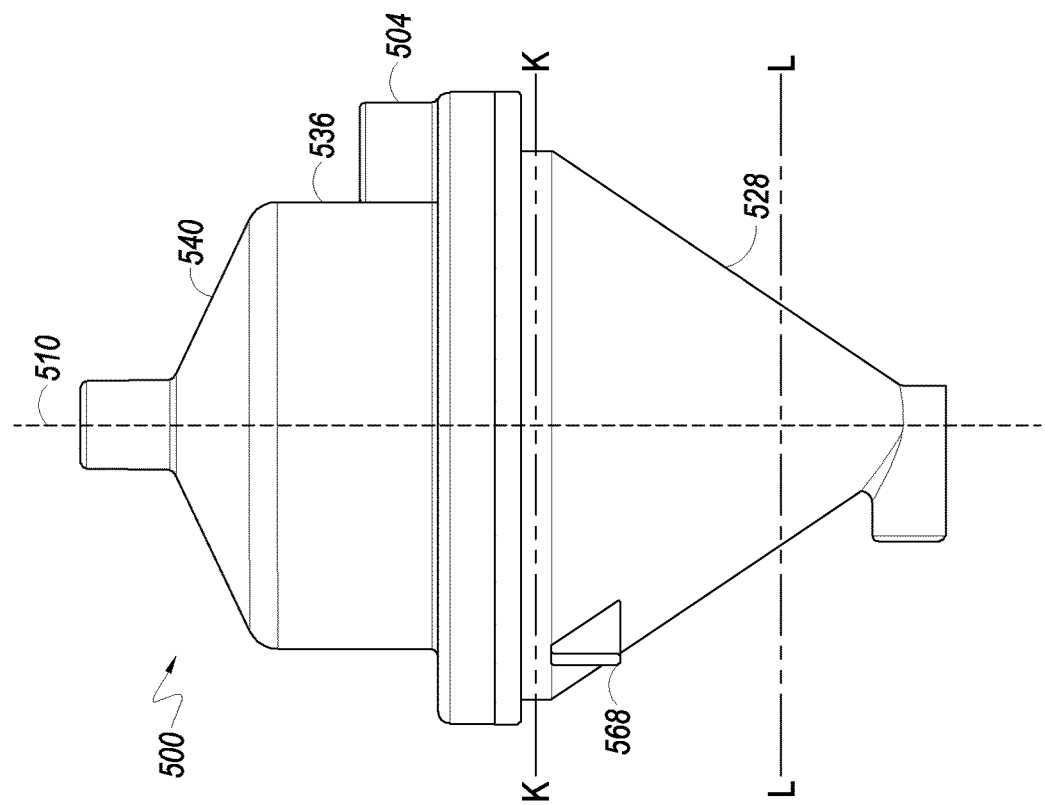
Figure 5B:
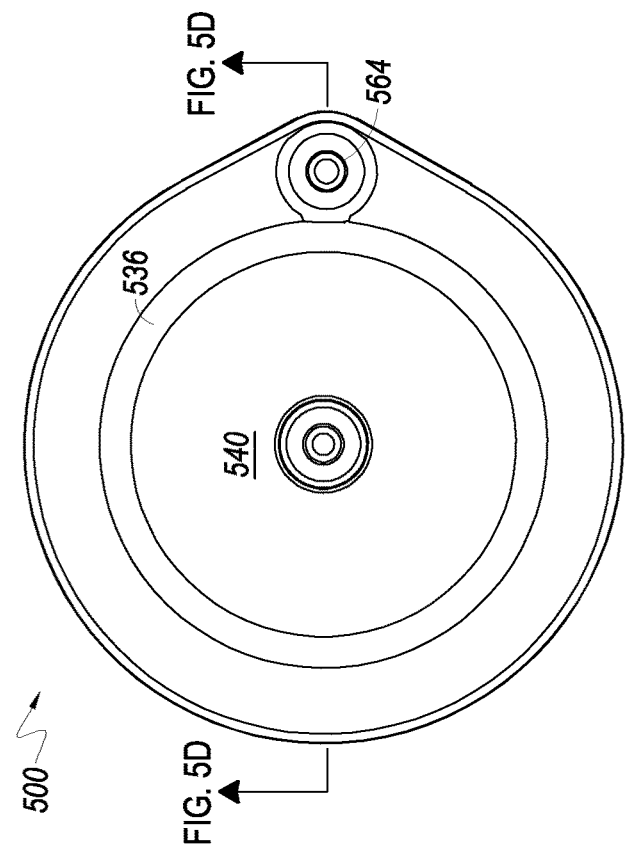
Figure 6A:
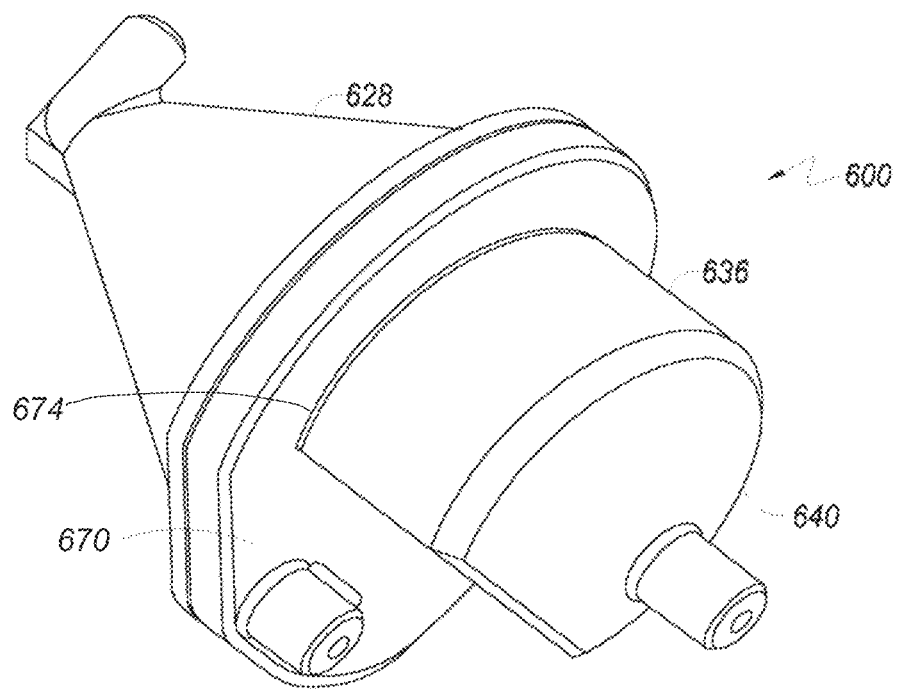
Figure 6D:
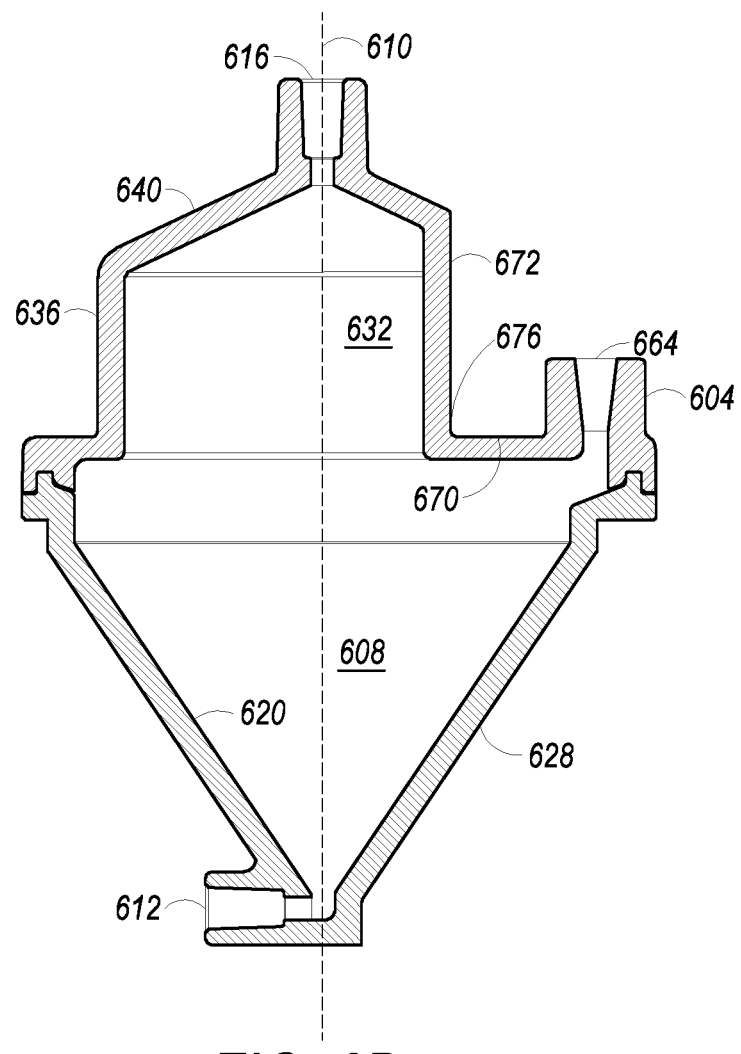

FIG. 5A illustrates a perspective view of chamber 500; FIG. 5B illustrates a top plan view of chamber 500; FIG. 5C illustrates a side elevation view of chamber 500; FIG. 5D illustrates a cross-sectional view of chamber 500; and FIG. 5E is a zoomed-in cross-sectional view around a port 504. In some embodiments, chambers consistent with the present invention, e.g., chamber 500, may be made from a single piece, e.g., a 3-D printed piece. In other embodiments, chambers may be made from more than one piece Referring to FIGS. 5A-E, chamber 500 includes, inter alia, three ports. As shown in FIG. 5D, chamber 500 includes cell-injection port 504, which is an entry port that allows liquid and particles to be introduced into a volume 508 and may be located near a first cross section of volume 508 (e.g., cross section of chamber through line KK in FIG. 5C). Inlet/evacuation port 512 is a port through which fluid is introduced into the chamber to maintain particles injected through port 504 in a fluidized bed and from which particles and some liquid are removed from volume 508 when sufficient particles have been collected or washed. The inlet port 512 may be located in a lower portion of volume 508, that is, at the apex of the frustro-conical chamber. In addition, outlet port 516 is an exit port through which liquid separated from the particles (in order to concentrate the particles in a smaller volume of liquid, wash the particles with the liquid, and/or treat the particles with the liquid) is removed. Outlet port 516 may be located in a top portion or base of frustro-conical chamber 500.

Chamber 500 also includes a sloped surface 520 that directs at least a portion of particles in volume 508 toward inlet port 512. Sloped surface 520 slopes toward inlet port 512. In operation, chamber 500 may be subjected to a force, e.g., gravity or centrifugal force that generally moves particles toward inlet port 512. Sloped surface 520 aids in directing particles toward inlet port 512 while allowing wash or replacement fluid to evenly flow around the particles thus suspending the particles in a fluidized bed, wherein the force of fluid flowing from inlet port 512 and the gravitational force acting on the particles balance.

One additional feature on chamber 500 is alignment aid 568 on side wall 528 (FIG. 5C). In embodiments, chamber 500 may be positioned on a centrifuge and alignment aid 568 may be used to ensure that when mounted on the centrifuge, chamber 500 is in a specific orientation.

Chamber 500 also includes side wall 528. Side wall 528 defines volume 508. Side wall 528 is angled with respect to central axis 510 defining volume 508 as generally frustro-conical or conical in shape, with a circular cross section such as cross sections at line KK or LL (FIG. 5C).

Chamber 500 also includes a second volume 532 which is located above volume 508. As illustrated in FIG. 5D, second volume 532 is defined by a side wall 536 and a top wall 540. As shown in FIG. 5D, outlet port 516 is located in top wall 540.

In some embodiments, the addition of a second volume may improve the processing of particles. For example, in one embodiment of processing cells, the additional volume provided by second volume 532 allows a larger number (e.g., volume) of cells to be processed in chamber 500. The additional volume may also be useful in embodiments where the cells may be washed, so that the wash liquid, which may be introduced through port 512 has room to flow through the cell bed in the lower portion of volume 508 and any cells carried into volume 532 have time to settle back into volume 508 instead of immediately exiting through port 516.

Top wall 540, which defines the second volume 532, may in some embodiments be substantially perpendicular to central axis 510, e.g., horizontal. Although as illustrated in FIGS. 5A-E, top wall 540 is angled toward inlet port 516. In some embodiments, the angle between top wall 540 and central axis 510 may be between about 90 degrees (e.g., top wall is horizontal) to about 5 degrees (e.g., top wall is steeply angled toward outlet port 516). In other embodiments, the angle between top wall 540 and central axis 510 may be between about 90 degrees and about 10 degrees, such as between about 80 degrees and about 15 degrees, or even between about 75 degrees and about 20 degrees.

Injection port 504 is in sidewall 528 as shown. Sloped surface 520 is provided by side wall 528 and slopes toward inlet port 512. Additionally, a portion of inlet port 512 is inside wall 528. FIG. 5E illustrates a zoomed-in cross-sectional view of the area near injection port 504. This area includes a number of features that may be used in some embodiments.

The injection port 504 may further include a sloped surface 552. The chamber 500 also includes a dam 556 (FIG. 5D). Referring again to FIG. 5E, a channel 554 is provided that is in fluid communication with the injection port 504. The channel 554 is at least partially defined by the dam 556. The channel 554 directs flow of particles and liquid away from injection port 504. The dam 554 is circumferentially disposed within the chamber 500 and forms the channel 554 between the dam 554 and the frustro-conical chamber 500. The dam 554 has its maximum height adjacent the injection port 504, and the height diminishes away from the injection port 504 on at least one side of the injection port 504 or on both sides thereof. The dam 554 may extend partially around the circumference of the chamber 500 or completely around the circumference, with the channel 554 ending at a point diametrically across the chamber 500 from the injection port 504 where the height of the dam 554 is zero. The height of the dam 556 may also decrease uniformly away from the cell-injection port 504.

In some embodiments, the injection port 504 is in fluid communication with an entry pathway 564 (FIGS. 5D and 5E) that directs flow of particles and liquid to the injection port 504. Cells and fluid entering the chamber 500 through the injection port 504 are guided by the dam 556 and channel 554 into the volume 508. The tapered shape of the dam 556 as described above produces improved flow characteristics over the configuration disclosed in US 2016/045921A1. In comparative testing a control chamber according to FIGS. 10A-E of US 2016/045921A1 lost 4.5% of injected cells during a startup phase of cell washing. In contrast, a chamber according to FIGS. 5A-E as described herein had only a 2.9% cell loss. Cell loss refers to cells injected through the injection port 504 and flushed through the outlet port 516 and consequently not recovered through the inlet port 512 when fluid flow is reversed and the washed cells are collected.

A second embodiment of the chamber is illustrated in FIGS. 6 A-D. In these figures, features described in connection with FIGS. 5 A-E with a five hundred number (e.g., inlet port 512) are designated with a six hundred number (e.g., inlet port 612). Since the features have similar functions they are not further described herein.

Additional features of this embodiment are a shelf 670 and a truncation wall 672. The shelf 670 adjacent the injection port 604 comprises an injection directing means. The shelf 670 extends into the interior of the chamber 600 from the injection port 604, thereby impeding fluid flow in the direction of the outlet port 616. The shelf 670 may be generally planar and may be coupled to the side wall 636 of the chamber 600 at a curved edge 674 of the shelf 670. The shelf 670 may be perpendicular to an axis 610 of the chamber 600. The shelf 670 may also comprise an interior edge 676 extending between two ends of the curved edge 674. The interior edge 676 may be straight. The chamber 600 may also comprise the truncation wall 672 coupled to the interior edge 676 of the shelf 670 and perpendicular to the shelf 670. The truncation wall 672 prevents cell-containing fluid from becoming trapped on a side of the shelf 670 facing the outlet port 616. The truncation wall 672 may be planar. Alternatively, the shelf 670 may protrude into the chamber 600 without removing a volume of the chamber 600 over the shelf 670.

The configuration of FIGS. 6A-D was also tested. The chamber according to FIGS. 6A-D as described herein had only a 2.0% cell loss during startup, which was a further improvement over the configuration of FIGS. 5A-E.

Figure 7:
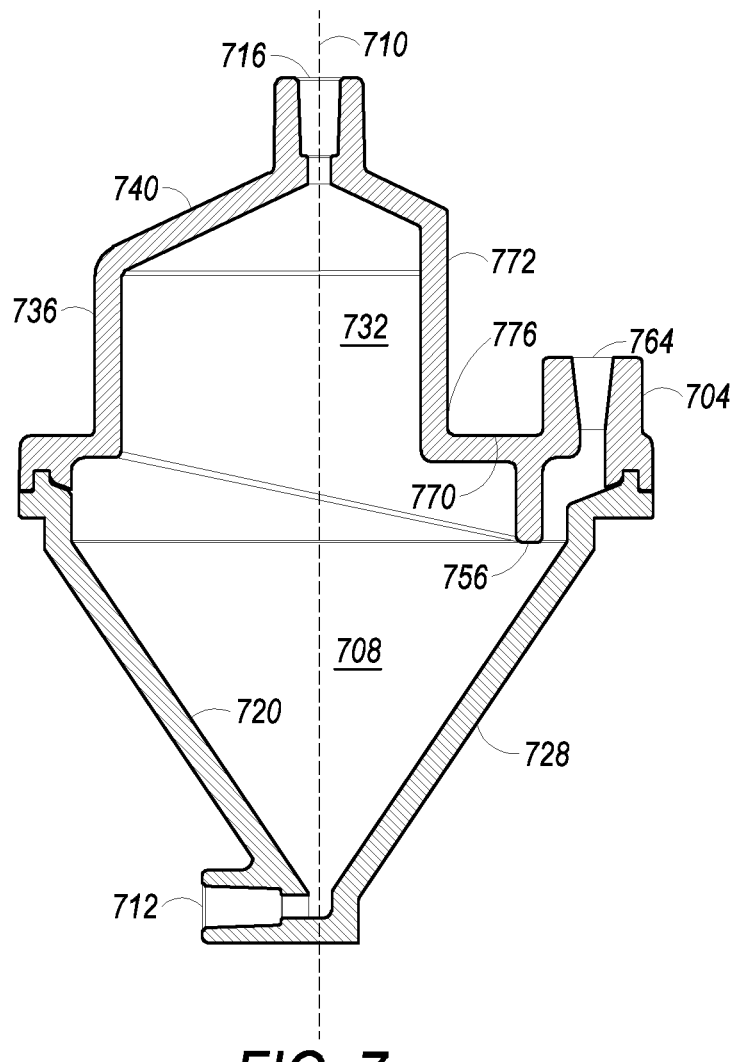
FIG. 7 illustrates a through sectional view of a chamber consistent with a third embodiment.

A third embodiment of the chamber is illustrated in FIG. 7. As before, in this figure, features described in connection with FIGS. 5 A-E with a five hundred number (e.g., inlet port 512) or in FIGS. 6A-D with a six hundred number are designated with a seven hundred number (e.g., inlet port 712). Since the features have similar functions they are not further described herein. The third embodiment is a combination of the tapered dam of the first embodiment and the shelf of the second embodiment.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the claimed invention.

What is claimed is:

1. A chamber for separating particles from a liquid, the chamber comprising:
   a first side wall defining a first volume, the first volume being frustro-conical;
   a second side wall defining a second volume located above the first volume;
   a first port in fluid communication with the first volume, wherein the first port is located at a junction between the first side wall and the second side wall;
   an injection-directing surface configured to direct inflowing fluid from the first port along a frustro-conical portion of the first side wall;

a second port in fluid communication with the first volume, wherein the second port is located at an apex of the first volume; and a third port in fluid communication with the second volume, wherein the third port is located in an upper portion of the second volume, above the second port; and a dam adjacent the first port, the dam including the injection-directing surface, and the dam configured to prevent flow of particles in liquid into the second volume, the dam at least partially defining a channel for flow of particles away from the second volume, the dam having a maximum height adjacent to the first port, and the dam diminishing in height away from the first port.

2. The chamber of claim 1, wherein the dam is circumferentially disposed within the chamber and forms a channel between the dam and a portion of the first side wall.

3. The chamber of claim 2, wherein the height of the dam diminishes away from the first port on at least one side of the first port.

4. The chamber of claim 3, wherein the height of the dam diminishes away from the first port on both sides of the first port.

5. The chamber of claim 4, wherein the dam extends partially around a circumference of the chamber.

6. The chamber according to claim 5, wherein the dam uniformly decreases in height away from the first port.

7. The chamber of claim 4, wherein the dam extends completely around a circumference of the chamber to a point diametrically across the chamber from the first port, at which point the height of the dam is zero.

8. The chamber according to claim 7, wherein the dam uniformly decreases in height away from the first port.

9. The A chamber for separating particles from a liquid, the chamber comprising:
 a first side wall defining a first volume, the first volume being frustro-conical;
 a second side wall defining a second volume located above the first volume;
 a first port in fluid communication with the first volume, wherein the first port is located at a junction between the first side wall and the second side wall; an injection-directing surface configured to direct inflowing fluid from the first port along a frustro-conical portion of the first side wall;
 a second port in fluid communication with the first volume, wherein the second port is located at an apex of the first volume;
 a third port in fluid communication with the second volume, wherein the third port is located in an upper portion of the second volume, above the second port; and
 a shelf including the injection-directing surface, the shelf being generally planar and being perpendicular to an axis of the chamber, the axis being defined as a line from the second port to the third port.

10. The chamber according to claim 9 wherein the shelf extends into an interior of the chamber from the first port, thereby impeding fluid flow in a direction of the third port.

11. The chamber according to claim 10 wherein the shelf is coupled to the second side wall of the chamber at a curved edge of the shelf.

12. The chamber according to claim 9 wherein the shelf further comprises an interior edge.

13. The chamber according to claim 12 wherein the interior edge is straight.

14. The chamber according to claim 13 further comprising:
 a truncation wall coupled to the interior edge of the shelf and perpendicular to the shelf.

15. The chamber according to claim 14 wherein the truncation wall is planar.

16. The chamber of claim 10 further comprising:
 a dam adjacent the first port, the dam configured to prevent flow of particles in liquid into the second volume, wherein the dam at least partially defines a channel for flow of particles away from the second volume wherein the dam has a maximum height adjacent the first port and the dam diminishes in height away from the first port.

17. The chamber according to claim 16 further comprising:
 a truncation wall coupled to the shelf and perpendicular to the shelf.

18. The chamber of claim 16, wherein the height of the dam diminishes away from the first port on both sides of the first port.

19. The chamber of claim 16, wherein the dam uniformly decreases in height away from the first port.

* * * * *